United States Patent [19]

Heinrich et al.

[11] Patent Number: 4,629,816

[45] Date of Patent: Dec. 16, 1986

[54] PROCESS FOR THE PRODUCTION OF 2,3-DICHLOROBUTADIENE-(1,3)

[75] Inventors: Josef Heinrich, Langenfeld; Rudolf Casper, Leverkusen; Manfred Beck, Cologne, all of Fed. Rep. of Germany

[73] Assignee: Bayer Aktiengesellschaft, Leverkusen, Fed. Rep. of Germany

[21] Appl. No.: 471,183

[22] Filed: Mar. 1, 1983

[30] Foreign Application Priority Data

Mar. 11, 1982 [DE] Fed. Rep. of Germany ....... 3208796

[51] Int. Cl.$^4$ ............................................. C07C 17/34
[52] U.S. Cl. .................................... 570/229; 570/228
[58] Field of Search ................................ 570/229, 228

[56] References Cited

U.S. PATENT DOCUMENTS

| | | | |
|---|---|---|---|
| 3,639,493 | 2/1972 | Campbell | 570/229 |
| 3,755,476 | 8/1973 | Crary et al. | 570/229 |
| 3,896,181 | 7/1975 | Brown et al. | 570/229 |
| 4,035,429 | 7/1977 | Karapetian et al. | 570/229 |

FOREIGN PATENT DOCUMENTS

| | | | |
|---|---|---|---|
| 2545341 | 4/1977 | Fed. Rep. of Germany | 570/229 |
| 1347633 | 2/1974 | United Kingdom | 570/229 |
| 2088363 | 6/1982 | United Kingdom | 570/229 |

*Primary Examiner*—Natalie Trousof
*Assistant Examiner*—Joseph A. Boska
*Attorney, Agent, or Firm*—Connolly and Hutz

[57] ABSTRACT

2,3-Dichlorobutadiene-(1,3) is obtained from 2,3,4-trichlorobutene-1 by dehydrohalogenation in the presence of a phase transfer catalyst, an inhibitor and oxygen according to an improved process in which the aqueous solution of an alkali metal hydroxide is added to the mixture of trichlorobutene, catalyst, inhibitor and optionally water, and the reaction is carried out at a temperature of from −10° to +60° C. under an inert gas which contains from 0.1 to 8% by weight of oxygen.

10 Claims, No Drawings

PROCESS FOR THE PRODUCTION OF 2,3-DICHLOROBUTADIENE-(1,3)

This invention relates to an improved process for the production of 2,3-dichlorobutadiene-(1,3) by the dehydrochlorination of 2,3,4-trichlorobutene-1 using an aqueous-alkaline solution in the presence of phase transfer catalysts and polymerisation inhibitors.

Since 2,3,4-trichlorobutene-1 forms a two-phase system with aqueous alkalis, the dehydrochlorination takes place very slowly even with vigorous stirring, because the reaction can only take place at the phase interface. The rate of the reaction may be increased by converting the trichlorobutene and the hydrogen chloride acceptor into a homogeneous phase. Processes of this type are known and references are provided in DE-OS No. 2,545,341.

However, all the known processes have some serious disadvantages.

It is difficult to achieve a complete conversion, to separate the dichlorobutadiene and to obtain a high yield. The formation of polymer deposits particularly hinders the separation of the monomer and reduces the yield. It is stated in British Pat. No. 1,048,510 that the known stabilizers are incapable of completely stopping the spontaneous, undesired polymerisation of the dichlorobutadiene during the production thereof.

The phase transfer catalysts according to DE-AS No. 1,618,790 provided a substantial advance in catalytic dehydrochlorination reactions. The term "phase transfer catalysis" characterises reactions between substances in a two phase system which are accelerated by ammonium, phosphonium or sulphonium salts.

An attempt to produce 2,3-dichlorobutadiene-(1,3) according to the method described in German Pat. No. 1,618,790, the essential features of which are working under a nitrogen atmosphere, the use of a single inhibitor and the addition of trichlorobutene as the last reaction component to the mixture of the other mixture ingredients, does not, however, achieve the desired result. Considerable quantities of polymer deposits are formed during the reaction, even in the presence of the very effective inhibitor phenothiazine.

The reason for this considerable polymer formation is the known extreme polymerisation ability of 2,3-dichlorobutadiene-(1,3). The polymerisation rate of 2,3-dichlorobutadiene-(1,3) surpasses that of isoprene 2000 times. Thus, the stabilization of this monomer against spontaneous, undesired polymerisation under the conditions provided during the production thereof constituents a difficult problem.

A solution to this problem is described in DE-OS No. 2,545,341. In this publication, a certain reaction temperature range (from −10 to +60° C.) is observed and an aqueous solution of the phase transfer catalyst is added as the last reaction component. Highly concentrated solutions of the catalyst should not be used. Finally, the process is carried out in the presence of atmospheric oxygen and in the presence of an inhibitor combination.

In this manner, it is indeed possible to stop the spontaneous polymerisation of 2,3-dichlorobutadiene-(1,3), but the subsequent stirring times which are necessary once the phase transfer catalyst has been added and which, according to the Examples, last from 7 to 36 hours are disadvantageous for economic reasons. Moreover, for reasons of operational safety, it is hazardous to carry out a reaction with organic compounds in the presence of air (about 20% by volume of oxygen).

Surprisingly, it has now been found that the subsequent stirring times may be drastically curtailed by modifying the method of DE-OS No. 2,545,341 in that the aqueous solution of the alkali metal hydroxide is added as the last reaction component to the mixture of the other reaction components.

It has also been found that, by this variation, it is possible to restrict the necessary oxygen concentration in the atmosphere over the reaction mixture to values of below 8% by volume in order to avoid the spontaneous polymerisation of 2,3-dichlorobutadiene-(1,3), thereby ensuring operational safety, because, as is known, 8% by volume of oxygen in the gas phase is the limit for most organic compounds, below which there is no risk of an explosion.

Therefore, the present invention provides a process for the production of 2,3-dichlorobutadiene-(1,3) by the dehydrochlorination of 2,3,4-trichlorobutene-1 with an aqueous solution of an alkali metal hydroxide in the presence of at least one phase transfer catalyst, at least one inhibitor and oxygen, characterised in that the aqueous solution of an alkali metal hydroxide is added to the mixture of 2,3,4-trichlorobutene-1, the phase transfer catalyst, the inhibitor and optionally water, and the reaction is carried out at from −10° to +60° C. and under an inert gas which contains from 0.1 to 8% by volume of oxygen.

Literature references to known compounds which are suitable as catalyst are provided in DE-OS No. 2,545,341. Of the sulphonium, phosphonium and ammonium compounds which are included, phosphonium and ammonium compounds are preferred. These are peralkylated phosphonium and ammonium hydroxides or halides having a long chain alkyl substituent, such as tributyl-hexadecylammonium-bromide.

The quantity of catalyst required for dehydrochlorination depends considerably on the activity of the catalyst. In the case of very active catalysts, quantities of 0.05% by weight are sufficient, and in the case of less active catalysts, quantities of up to 10% by weight, based on 2,3,4-trichlorobutene, may be used.

Dehydrochlorination is preferably carried out at a temperature of from −5° to +25° C. The oxygen concentration in the inert gas phase over the reaction mixture is preferably from 0.2 to 2% by volume. Nitrogen is preferably used as the inert gas.

Working with an oxygen concentration of below 0.1% by volume results in an increasing polymer formation, which complicates working up and reduces the yield.

The quantity of water in the reaction mixture when carrying out the process of the present invention is not critical. The quantity of water necessary for dissolving the resulting alkali metal halide is to be considered as the lower limit. The upper limit is determined by the dilution of the alkali metal hydroxide which is used.

The concentration of the alkali metal hydroxide solution used is preferably from 20 to 50% by weight. The mol ratio of 2,3,4-trichlorobutene-1 to alkali metal hydroxide is from 1:1.05 to 1:1.5.

Sodium hydroxide is preferably used as the alkali metal hydroxide.

A particularly advantageous variant of the present process comprises introducing water with the other reaction components and adding sodium hydroxide in the form of a 50% by weight aqueous sodium hydroxide which is available commercially, so that the effective concentration of sodium hydroxide is always low due to the dilution in the reaction medium. Consequently, a very smooth reaction course is achieved, without resulting in prolongation of the duration of reaction.

From 15 to 100% weight of water, based on trichlorobutene, are preferably introduced.

The 2,3-dichlorobutadiene-(1,3) which results during the reaction is stabilized by polymerisation inhibitors. Suitable inhibitors originate from the class of amines, such as phenothiazine or piperazine, from the class of hydroxylamines, such as diethylhydroxylamine, or from the class of N-nitroso compounds, such as N-nitrosodiphenylamine.

The inhibitors are used in quantities of from 50 to 10 000 ppm, preferably from 100 to 1 000 ppm, based on 2,3,4-trichlorobutene-1.

Dehydrochlorination is carried out up to a conversion of more than 99.9% of the starting compound, so that the resulting 2,3-dichlorobutadiene-(1,3) contains less than 0.1% by weight of 2,3,4-trichlorobutene-1. The virtual 100% conversion of the starting compound which is desired is achieved by a suitable choice of the duration of reaction or of the residence time, depending on whether a continuous or discontinuous method is employed. The 2,3-dichlorobutadiene-(1,3) is separated by phase separation in a separating vessel. In a continuous process, the dichlorobutadiene is preferably separated in a horizontal separating flask. For a rapid phase separation, it is particularly advantageous to pass the reaction mixture through a glass wool filter before separation. In addition thereto, other known separating processes, such as extraction or distillation, may also be used.

2,3-Dichlorobutadiene-(1,3) is used for the production of polymers which serve as adhesives, specifically in rubber and metal bonding. It is used as a comonomer in the production of types of crystallisation-disturbed polychloroprene, in which case rubbers are obtained which still have good elastic properties even at low temperatures.

The apparatus used in the following Examples comprises a cylindrical 6 liter glass flask having a jacket and provided with a grid stirrer, a dropping funnel, a thermometer and a gas inlet. A stopcock is provided at the bottom of the vessel to draw off the liquids.

The air in the apparatus was expelled by nitrogen, and a mixture of 0.5% by volume of oxygen and 99.5% by volume of nitrogen was then passed over the reaction mixture.

The conversion of 2,3,4-trichlorobutene-1 (TCB) was followed by gas chromatography.

Bis-(2-hydroxy-propyl)-benzyl-hexadecylammonium chloride was used as the phase transfer catalyst.

EXAMPLE 1

1840 g of TCB, 1.5 g of catalyst, 0.8 g of phenothiazine and 0.1 g of N-nitrosodiphenylamine were introduced into the apparatus. After cooling to 12° C., 566 g of NaOH, dissolved in 2264 g of water were added dropwise with vigorous stirring so that the temperature did not rise above 14° C. The mixture was then stirred for 3 hours and the 2,3-dichlorobutadiene-(1,3) (DCB) which still contained 0.4% by weight of TCB was isolated. No polymeric DCB was produced while working up.

EXAMPLE 2

The process was carried out according to Example 1, but with 1 g of diethylhydroxylamine instead of the inhibitors phenothiazine and N-nitrosodiphenylamine.

After a subsequent stirring time of 3 hours, the conversion amounted to more than 99.9%. Polymers were not detected.

EXAMPLE 3

The process was carried out according to Example 1, but with 1 g of piperazine instead of the inhibitors used in Example 1.

After a subsequent stirring time of 3 hours, the TCB conversion amounted to more than 99.9%. Polymeric DCB had not been produced.

EXAMPLE 4

1840 g of TCB, 1.5 g of catalyst. 0.8 g of phenothiazine, 0.1 g of N-nitrosodiphenylamine and 1700 ml of water were introduced. After cooling to 12° C., 566 g of NaOH, dissolved in 566 g of water, were added dropwise with vigorous stirring so that the internal temperature did not rise above 14° C. The mixture was subsequently stirred for 4 hours. The isolated DCB contained 0.09% by weight of TCB. No polymeric DCB was produced while working up.

EXAMPLE 5

1840 g of TCB, 1.5 g of catalyst, 0.8 g of phenothiazine, 0.1 g of N-nitrosodiphenylamine and 300 ml of water were introduced. After cooling to 12° C. 566 g of NaOH, dissolved in 566 g of water, were added dropwise with vigorous stirring, so that the temperature did not rise above 14° C.

The mixture was subsequently stirred for 4 hours. The TCB conversion amounted to more than 99.9%. Polymers could not be detected.

1400 ml of water were added for working up.

COMPARATIVE EXAMPLE A 566 g of NaOH, 2264 g of water, 1.5 g of catalyst, 0.8 g of phenothiazine and 0.1 g of N-nitrosodiphenylamine were introduced. After cooling to 12° C., 1849 g of TCB were added dropwise with vigorous stirring, so that the internal temperature did not rise above 14° C.

After a subsequent stirring time of 4 hours, the experiment was interrupted.

The residual TCB content in the DCB was still 10.3% by weight. A small quantity of polymers had deposited at the phase interface complicating the phase separation.

COMPARATIVE EXAMPLE B 137.5 g of NaOH, 1000 g of water, 500 g of TCB, 0.5 g of phenothiazine, 0.2 g of N-nitrosodiphenylamine and 0.5 g of diethylhydroxylamine were introduced.

After cooling to 12° C., 0.5 g of catalyst in a 1% aqueous solution were added in such a way that the temperature did not rise above 14° C.

After subsequent stirring time of 12 hours, the experiment was interrupted. The residual content of TCB in the DCB was still 0.3%. Small quantities of polymers which, based on the theoretical DCB yield, made up about 1% by weight complicated the working up of the reaction mixture.

COMPARATIVE EXAMPLE C 1840 g of TCB, 1.5 g of catalyst, 0.8 g of phenothiazine and 0.1 g of N-nitrosodiphenylamine were introduced into the experimental apparatus.

The atmospheric oxygen in the reaction vessel was expelled by nitrogen, 200 ppm by volume of oxygen were then metered into the nitrogen, in contrast to the previously mentioned Examples.

After cooling to 12° C., 566 g of NaOH, dissolved in 2264 g of water, were metered in with vigorous stirring, so that the internal temperature did not rise above 14° C.

After a subsequent stirring time of 3 hours, the residual TCB content in the DCB amounted to 0.09% by weight. 10.4 g of polymers were isolated.

We claim:

1. A process for the production of 2,3-dichlorobutadiene-(1,3) by the dehydrochlorination of 2,3,4-trichlorobutene-1 with an aqueous solution of an alkali metal hydroxide in the presence of at least one phase transfer catalyst, at least one inhibitor and oxygen, characterised in that the aqueous solution of an alkali metal hydroxide is last added to the mixture of the 2,3,4-trichlorobutene-1, the phase transfer catalyst, the inhibitor and optionally water, and the reaction is carried out at from −10° to +60° C. under an inert gas which contains from 0.1 to 8% by volume of oxygen.

2. A process according to claim 1, characterised in that the phase transfer catalysts are peralkylated phosphonium or ammonium hydroxides or halides.

3. A process according to claim 1, characterised in that the catalyst is used in quantities of from 0.05 to 10% by weight, based on trichlorobutene.

4. A process according to claim 1, characterised in that the reaction is carried out at from −5° to +25° C.

5. A process according to claim 1, characterised in that the reaction is carried out under nitrogen which contains from 0.2 to 2% by volume of oxygen.

6. A process according to claim 1, characterised in that a 20 to 50% by weight alkali metal hydroxide solution is used and the mol ratio of trichlorobutene to alkali metal hydroxide is from 1:1.05 to 1:1.5.

7. A process according to claim 1, characterised in that the inhibitor is used in a quantity of from 50 to 10 000 ppm, based on trichlorobutene.

8. A process according to claim 1, characterised in that from 15 to 100% by weight of water, based on trichlorobutene, are introduced with the other reaction components, and the alkali metal hydroxide is added as a 50% by weight aqueous solution.

9. A process according to claim 1, characterised in that the alkali metal hydroxide is sodium hydroxide.

10. A process according to claim 7 wherein the amount of inhibitor is from 100 to 1000 ppm, based on trichlorobutene.